US00PP21391P2

(12) United States Plant Patent
Herring et al.

(10) Patent No.: US PP21,391 P2
(45) Date of Patent: Oct. 19, 2010

(54) *NANDINA DOMESTICA* PLANT NAMED 'MURASAKI'

(50) Latin Name: *Nandina domestica*
Varietal Denomination: Murasaki

(75) Inventors: April Herring, Houston, TX (US); Kay Herring, Tomball, TX (US); Josefina Herrera, Cypress, TX (US)

(73) Assignee: TNM Corporation, Waller, TX (US)

( * ) Notice: Subject to any disclaimer, the term of this patent is extended or adjusted under 35 U.S.C. 154(b) by 11 days.

(21) Appl. No.: 12/387,924

(22) Filed: May 8, 2009

(51) Int. Cl.
*A01H 5/00* (2006.01)

(52) U.S. Cl. ..... Plt./235

(58) Field of Classification Search ..... Plt./235
See application file for complete search history.

(56) References Cited

U.S. PATENT DOCUMENTS

PP14,668 P3 4/2004 Rushing

*Primary Examiner*—Kent L Bell
(74) *Attorney, Agent, or Firm*—Christie, Parker & Hale, LLP

(57) ABSTRACT

'MURASAKI', a new and distinct variety of *Nandina domestica*, characterized by its tight, dense mounding plant habit spreading slowly through underground rhizomes with age; slow growth rate; and unique wine-red-colored young foliage and deep grey green-colored mature foliage. Wine red color of young foliage is retained while the plant is actively growing.

10 Drawing Sheets

Classification: The present invention relates to a new *Nandina domestica* plant.

Variety denomination: The new plant has the varietal denomination 'MURASAKI'.

BACKGROUND OF THE INVENTION

The present invention relates to a new and distinct cultivar of *Nandina* plant, botanically known as *Nandina domestica*, a member of the Berberidaceae family, commonly known as Heavenly Bamboo.

This new 'MURASAKI' variety resulted from a naturally occurring, whole plant mutation discovered in a cultivated planting of the *Nandina domestica* variety 'Harbour Dwarf' (not patented). 'MURASAKI' appeared different from 'Harbour Dwarf' plants growing in stage 3 rooting culture in a plant micropropagation lab in Magnolia, Tex. and was initially discovered around December 2005 by the inventors.

The selection of this plant was based on its unique and long-lasting wine red-colored young foliage in contrast to the typical lime green-colored young foliage of the cultivar *Nandina domestica* 'Harbour Dwarf' (not patented).

The new variety was first reproduced by asexual propagation (micropropagation) in, Magnolia, Tex. It has since been reproduced numerous times at Magnolia, Tex. by asexual propagation (micropropagation). Using this method of asexual propagation it takes 2-3 weeks to initiate root development. Each of the progeny exhibit identical characteristics to the original mutant plant, showing that the unique features of this new *Nandina* are stable and reproduced true to type in successive generations.

SUMMARY OF THE INVENTION

Plants of the new *Nandina* have not been observed under all possible environmental conditions. The phenotype may vary somewhat with variations in environment such as temperature, daylength, light intensity, nutrition and water status without, however, any variance in genotype. The following observations and descriptions are of 2-year-old plants grown in a landscape in Magnolia, Tex.

The following traits have been repeatedly observed and are determined to be the unique characteristics of 'MURASAKI'. These characteristics in combination distinguish 'MURASAKI' as a new and distinct cultivar:

1. Dense, compact and mounding plant habit.
2. With age will spread through underground rhizomes.
3. Slow growth rate.
4. Unique wine red colored young foliage and deep grey green-colored mature foliage. Wine red color of young foliage is retained while the plants are actively growing.

The 'MURASAKI' cultivar has been observed and extensively tested in different growing situations for two years. Its recognizable characteristics, which distinguish it from other known *Nandina* cultivars are: 1) compact, dense form, with a mature height of 12-20"; 2) slow growth rate; 3) has proven adaptable to harsh environmental conditions; 4) flowers have been observed but no fruit has been observed to date; 5) exhibits unique leaf coloration—new growth is wine red, mature winter foliage is bronze red; and 6) is sun and shade tolerant maintaining its proportions equally well in both conditions.

COMPARISON WITH PARENT

The parent cultivar to the new *Nandina* is the cultivar 'Harbour Dwarf' (not patented). Plants of the new *Nandina* may be distinguished from the cultivar 'Harbour Dwarf' by the following combination of characteristics as seen in side-by-side comparisons conducted in Magnolia Tex. Plants of the new *Nandina* differed from plants of the cultivar 'Harbour Dwarf' primarily in developing foliage coloration as plants of the new *Nandina* produced wine red-colored leaves whereas plants of the cultivar 'Harbour Dwarf' produced lime green-colored leaves. It has also been observed that plants of the new *Nandina* produce a deep grey green colored mature foliage, Greyed-Green Group 189A, whereas plants of the cultivar 'Harbour Dwarf' produce a deep green colored mature foliage, Green Group 136A.

COMPARISON WITH THE CLOSEST COMMERCIALLY AVAILABLE CULTIVAR

The closest commercially available cultivar to the new *Nandina* is the cultivar 'Jaytee' (disclosed in U.S. Plant Pat. No. 14,668). Plants of the new *Nandina* differed from plants of the cultivar 'Jaytee' primarily in developing foliage coloration as plants of the new *Nandina* produced wine red-colored leaves, Greyed-Purple group 187A, whereas plants of the cultivar 'Jaytee' produced bronze-colored leaves, Greyed Orange group 174A. It has also been observed that plants of the cultivar 'Jaytee' produce abundant fruit whereas plants of the new *Nandina* have not produced fruit to date.

BRIEF DESCRIPTION OF ILLUSTRATIONS

FIG. 1-A is a photograph of the original plant 'MURASAKI' growing in a 72 cell tray with the 'Harbour Dwarf' crop it was found with at 3 months of age.

FIG. 1-B represents the same plants as FIG. 1-A, but 5 months later in a 3 gallon container.

FIG. 2-A is a side-by-side comparison of the new variety, shown on the left, with a 'Harbour Dwarf' shown on the right to illustrate the difference in color of the new growth. Both plants are in a 3 gallon container.

FIG. 2-B is a side-by-side comparison of the new variety, shown on the top of the frame, with a 'Harbour Dwarf' shown on bottom half of the frame. Both plants are in a landscape setting at approximately 12 months of age.

FIG. 2-C is a side-by-side comparison of the new variety, shown on the left, with a 'Harbour Dwarf' shown on the right to illustrate the difference in mature leaf color. Both plants are in a 3 gallon container.

FIG. 2-D is a side-by-side comparison of the new foliage of the new variety, shown on the left, with the new foliage of 'Harbour Dwarf' shown on the right.

FIG. 3-A is a side-by-side comparison of the new variety, shown on the left, with a 'Jaytee' shown on the right to illustrate the difference in color of the new growth. Both plants are in a 3 gallon container.

FIG. 3-B is a side-by-side comparison of the new foliage of the new variety, shown on the left, with the new foliage of 'Jaytee' shown on the right.

FIG. 4-A is a photograph of the new variety at 2 years old growing in a landscape setting in Magnolia, Tex. This photo shows the unique leaf coloration in the spring.

FIG. 5-A is a close up photograph of flower of the new variety.

DETAILED BOTANICAL DESCRIPTION

In the following description, color references are made to The Royal Horticultural Society Colour Chart except where general terms of ordinary dictionary significance is used. The following observations and measurements describe plants grown in a landscape setting in Magnolia, Tex.

Botanical classification: *Nandina domestica* cultivar 'MURASAKI'.

Parentage: A naturally occurring, whole plant mutation origianting in an asexually produced (micropropagated) population of *Nandina domestica* 'Harbour Dwarf' (not patented).

Propagation:

*Type.*—By tissue culture or micropropagation.

*Rooting habit.*—Numerous, fibrous, root initiation seen in 2-3 weeks.

Plant description:

*Appearance.*—Dwarf, dense, compact mounding form. Slow in growth with a spreading habit through underground rhizomes with age, and unique foliage coloration.

Mature plant height: 12-20 inches.

Mature plant width: 14-18 inches.

Stems:

*Stem diameter.*—6-8 mm.

*Internode length.*—15-20 mm.

*Stem color.*—Young Stems: Closest to Greyed-Green Group 189A. Mature Stems: Closest to Brown Group 200C.

*Stem length.*—12-15 cm.

*Stem form.*—Upright.

*Stem texture.*—Smooth, longitudinally ridged.

*Branching habit.*—Branches freely from the basal buds.

Foliage description: Evergreen.

*Arrangement.*—Alternate, Odd tripinnately Compound.

*Leaf length.*—27-35 cm.

*Leaf width.*—45-53 cm.

*Petiole diameter.*—1-2 mm.

*Petiole length.*—2-4 cm.

*Petiole color.*—Petioles on Young Foliage: Closest to Greyed-Orange Group 166A. Petioles on Intermediate Foliage: Greyed-Green Group 189A. Petioles on Mature Foliage: Closest to Greyed-Green Group 189A.

*Petiolule diameter.*—1 mm on average.

*Petiolule length.*—1 mm on average.

*Petiolule color.*—Petiolules on Young Foliage: Greyed-Orange Group 166A. Petiolules on Intermediate Foliage: Greyed-Green Group 189A. Petiolules on Mature Foliage: Closest to Greyed-Green Group 189A.

Leaflets:

*Leaflet base.*—Cuneate. Leaflet tips — Acute.

*Leaflet shape.*—Lanceolate.

*Leaflet margin.*—Entire.

*Leaflet venation pattern.*—Pinnate.

*Leaflet length.*—3-6 cm.

*Leaflet width.*—1-2 cm.

*Leaflet texture.*—Upper surface: Glaborous. Lower surface: Glaucous.

*Leaflet aspect.*—Cupped or reflexed.

Color:

*Young leaflets.*—Upper Side: Closest to Greyed-Purple Group 187A. Lower Side: Closest to Greyed-Orange Group 166A.

*Intermediate leaflets.*—Upper Side: Closest to Greyed-Orange Group 166A. Lower Side: Closest to Greyed-Green Group 189A.

*Mature leaflets.*—Upper Side: Closest to Greyed-Green Group 189A. Lower Side: Closest to Greyed-Green Group 189A. Winter color: Closest to Greyed-Purple Group 187A.

*Vein color.*—Veins on Young Leaflets: Greyed-Orange Group 166A. Veins on Intermediate Leaflets: Greyed-Green Group 189A. Veins on Mature Leaflets: Closed to Greyed-Green Group 189A.

*Inflorescence.*—Inflorescence is typical of the variety *Nandina domestica* 'Harbour Dwarf' (not patented).

*Description.*—Inflorescence borne on terminal erect stalked panicles, consisting of 40 to 160 individual perfect flowers. Inflorescence conical in shape. Individual flowers, actinomorphic with 6 white petals. Closest to White Group 155B. Petals are elliptic with an entire margin.

*Inflorescence bud.*—Length: 6-7 mm. Diameter: 3-5 mm. Closest to White Group 155A.

*Inflorescence size.*—Panicle. — Height: About 10-16 cm. Width: About 7-10 cm.

*Individual flower.*—Diameter about 1 cm. Petals. — Length: 5 mm. Width: 3-4 mm.

*Reproductive organs.*—Androecium. — 6 stamens. Length about 3 mm. Closest to Yellow Group 15A. The filament is insignificant as to be not visible. Gynoecium. — Pistil superior. Length about 4 mm. Width about 1-2 mm.

*Ovary.*—Color Closest to Orange-White Group 159C.

*Style.*—Color Closest to Orange-White Group 159D.

*Stigma.*—Closest to Orange Group 29A.

*Blooming duration.*—10 to 12 days.

*Bloom lastingness.*—1 to 4 days. Fragrance: None.

Seed production: To date, production of berries or seeds has not been observed.

Disease resistance: Resistance to diseases common to plants of *Nandina* has not been observed.

Pest resistance: Resistance to pests common to plants of *Nandina* has not been observed.

We claim:

1. A new and distinct cultivar of *Nandina domestica* plant named 'MURASAKI', as illustrated and described.

* * * * *

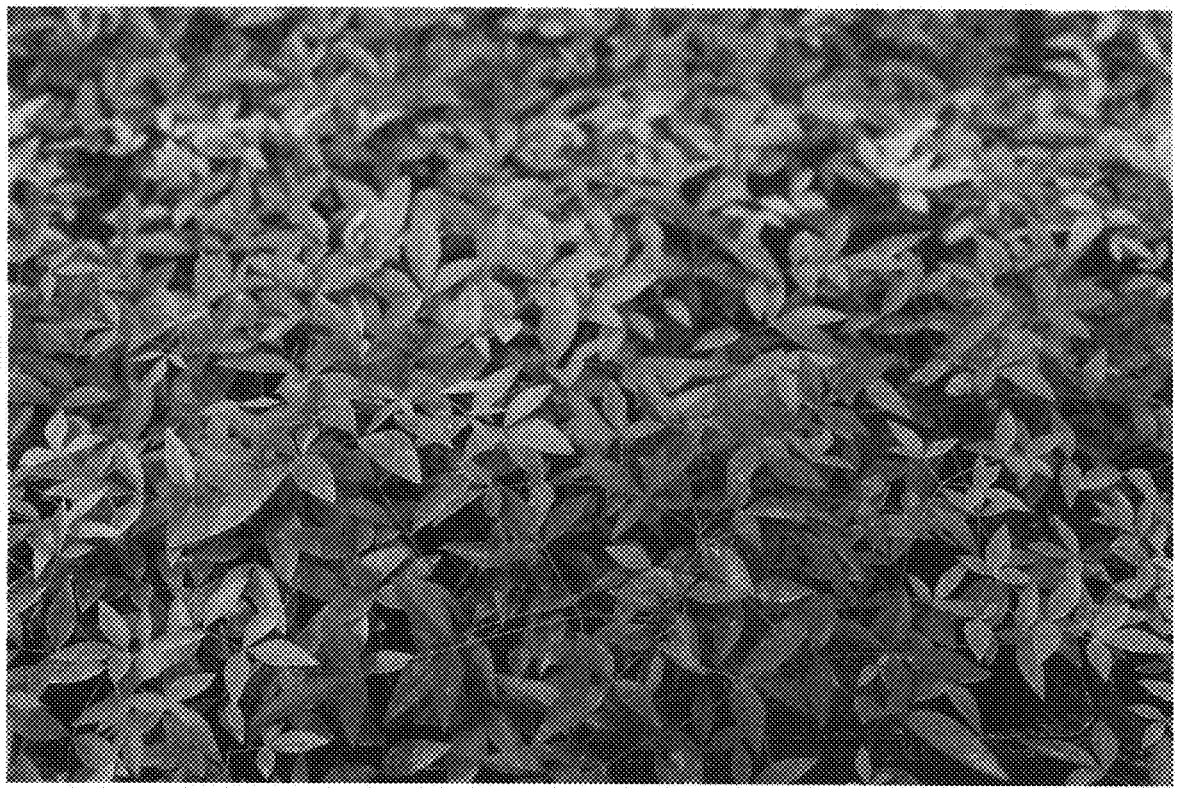
FIG. 1-A

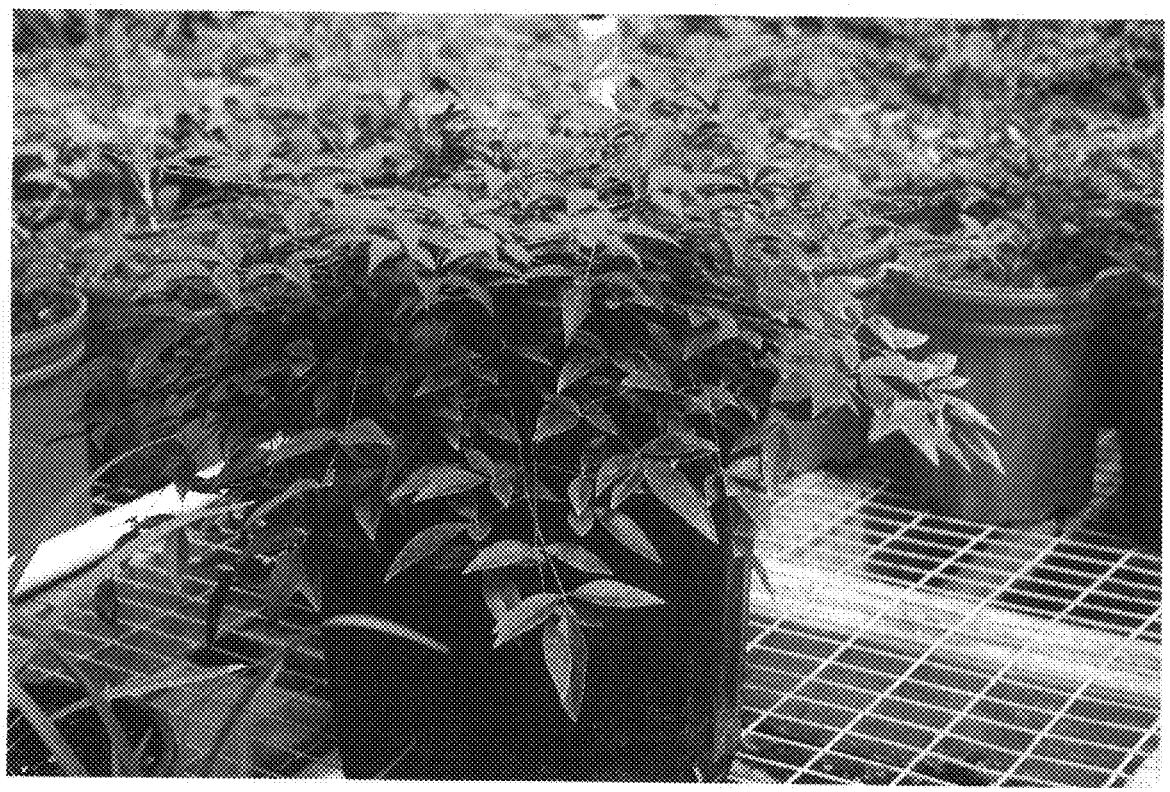
FIG. 1-B

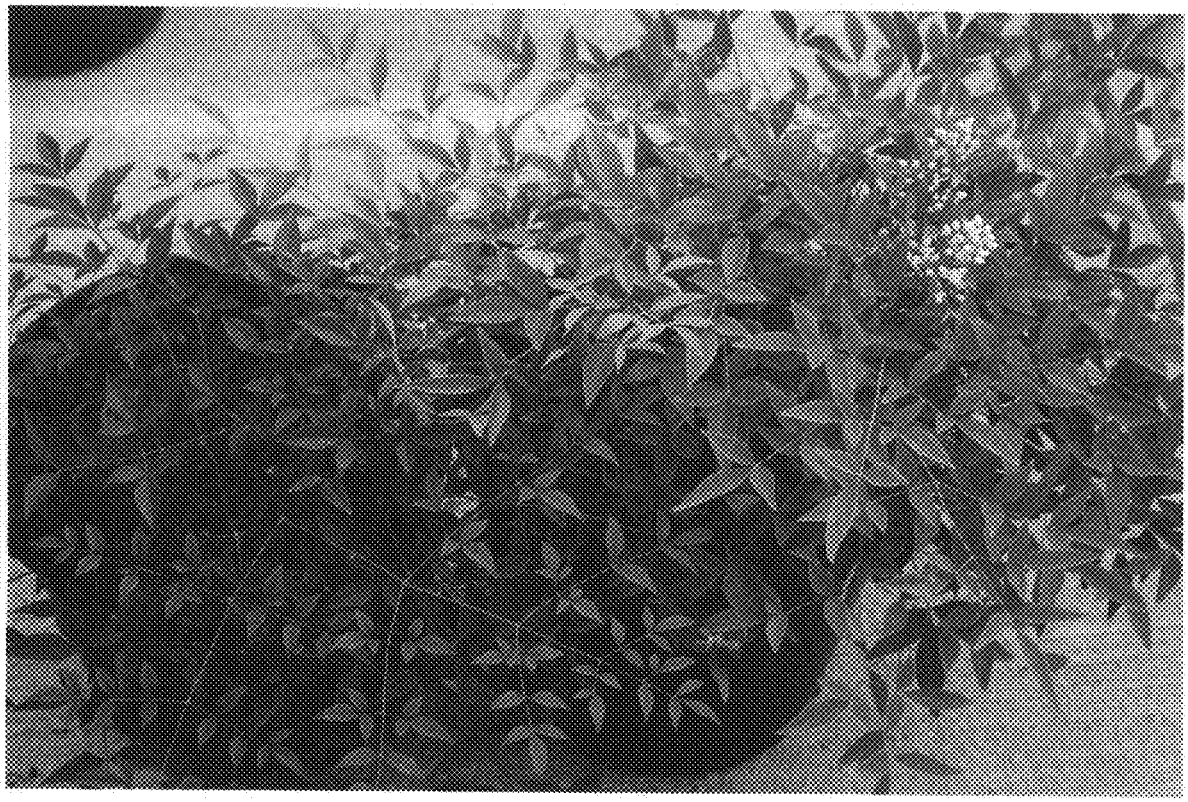
FIG. 2-A

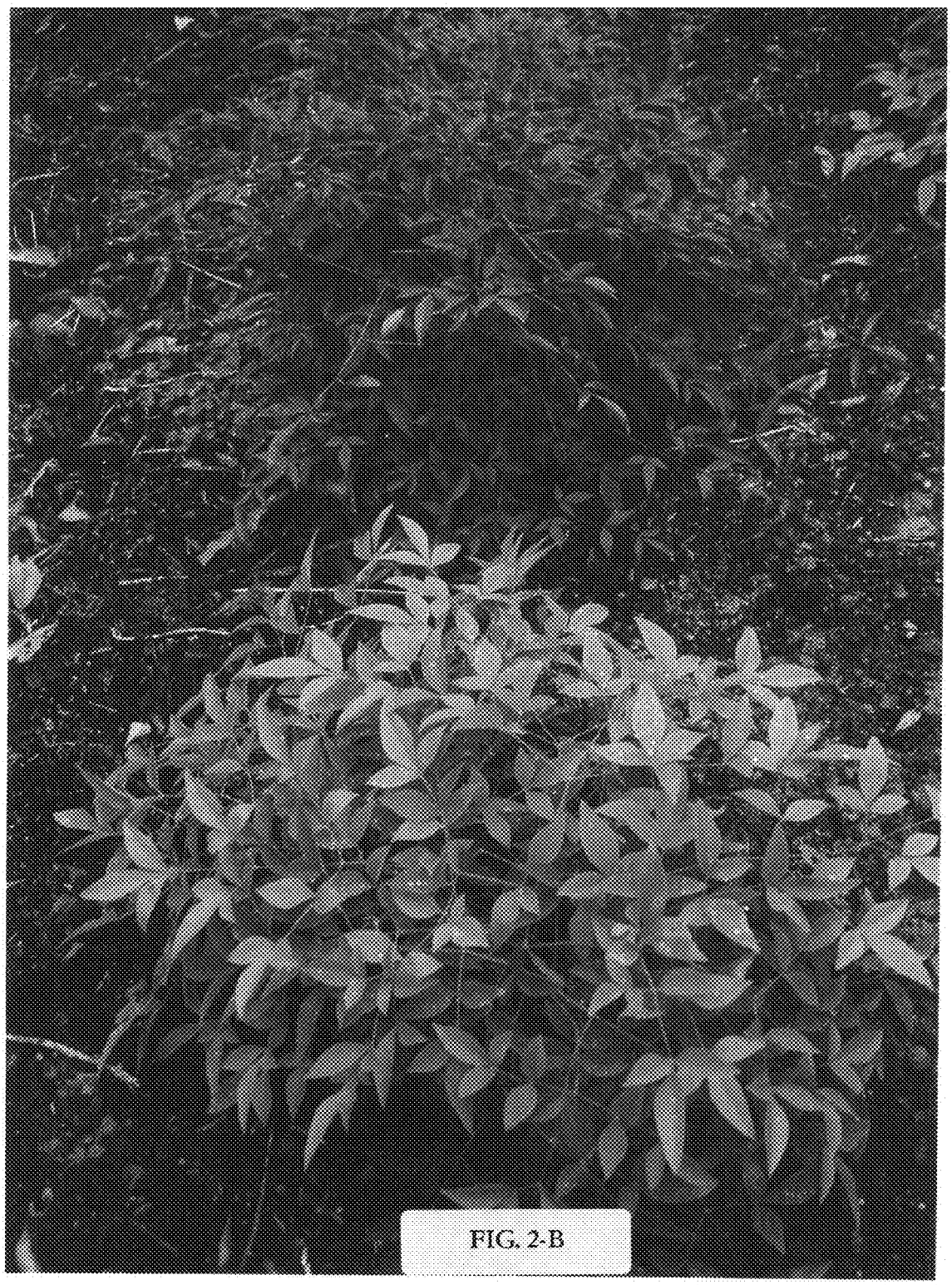
FIG. 2-B

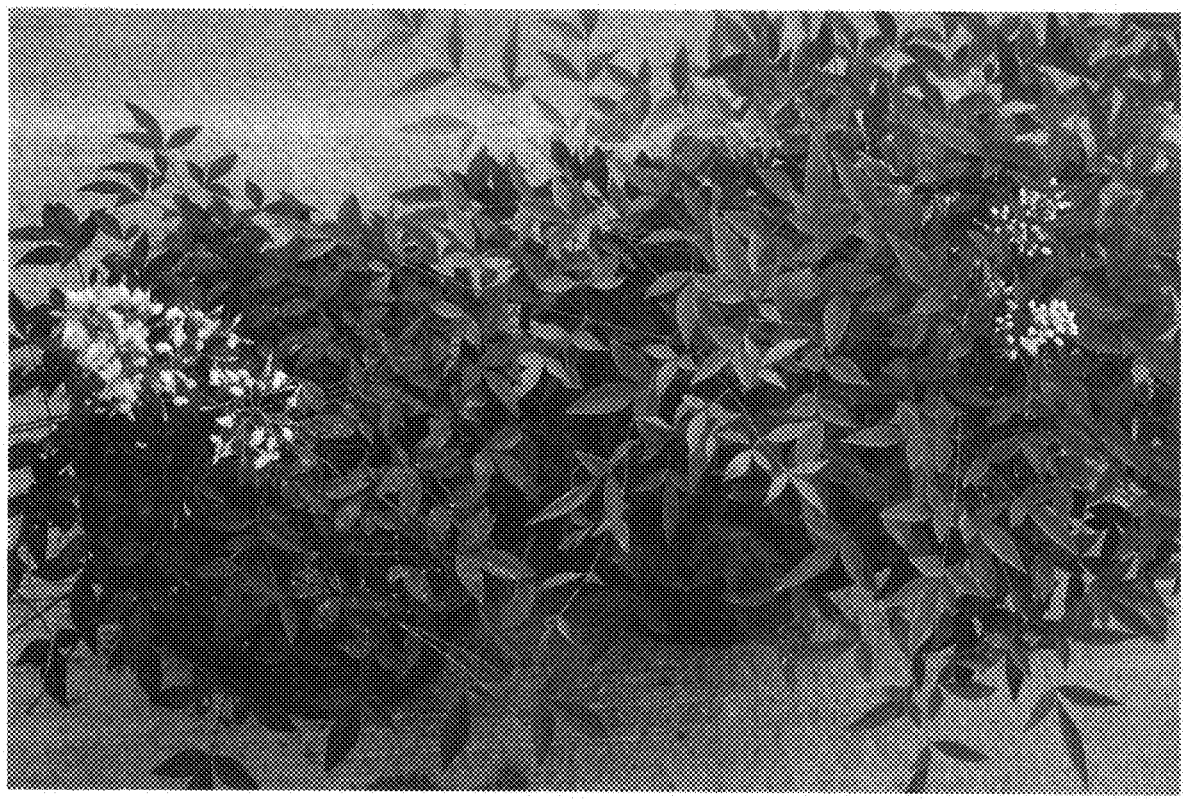
FIG. 2-C

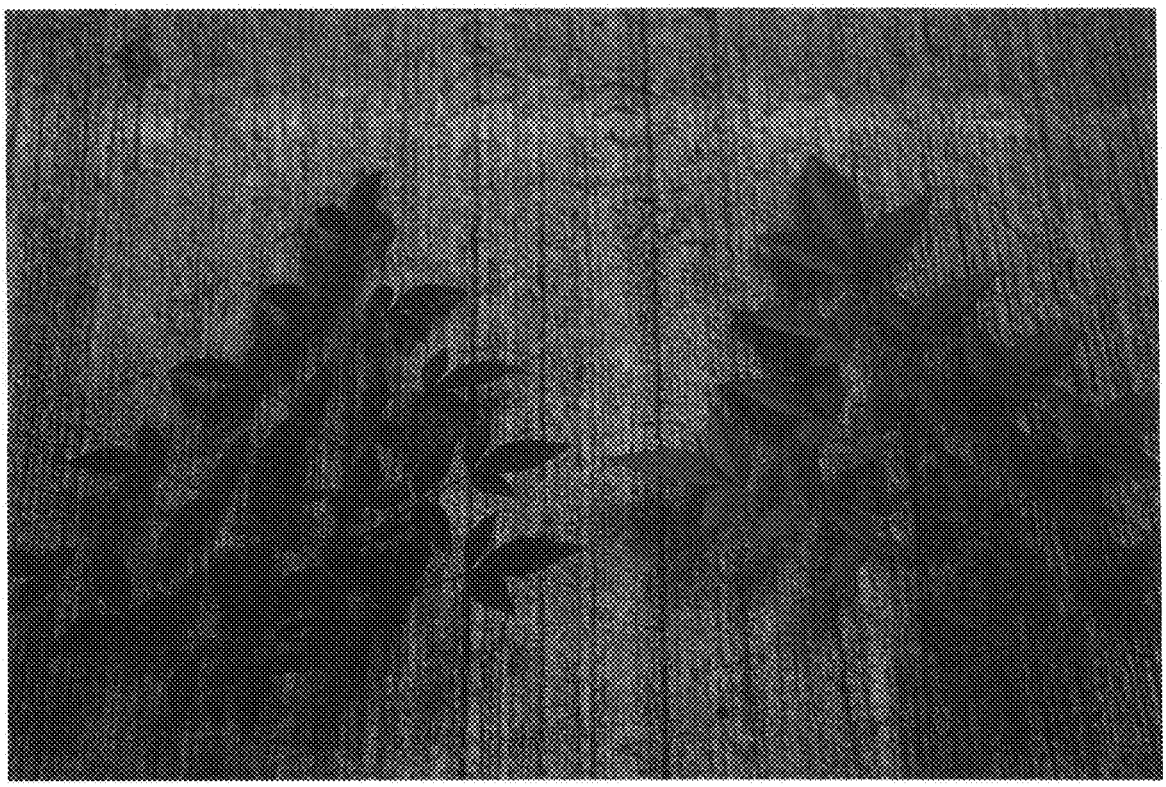
FIG. 2-D

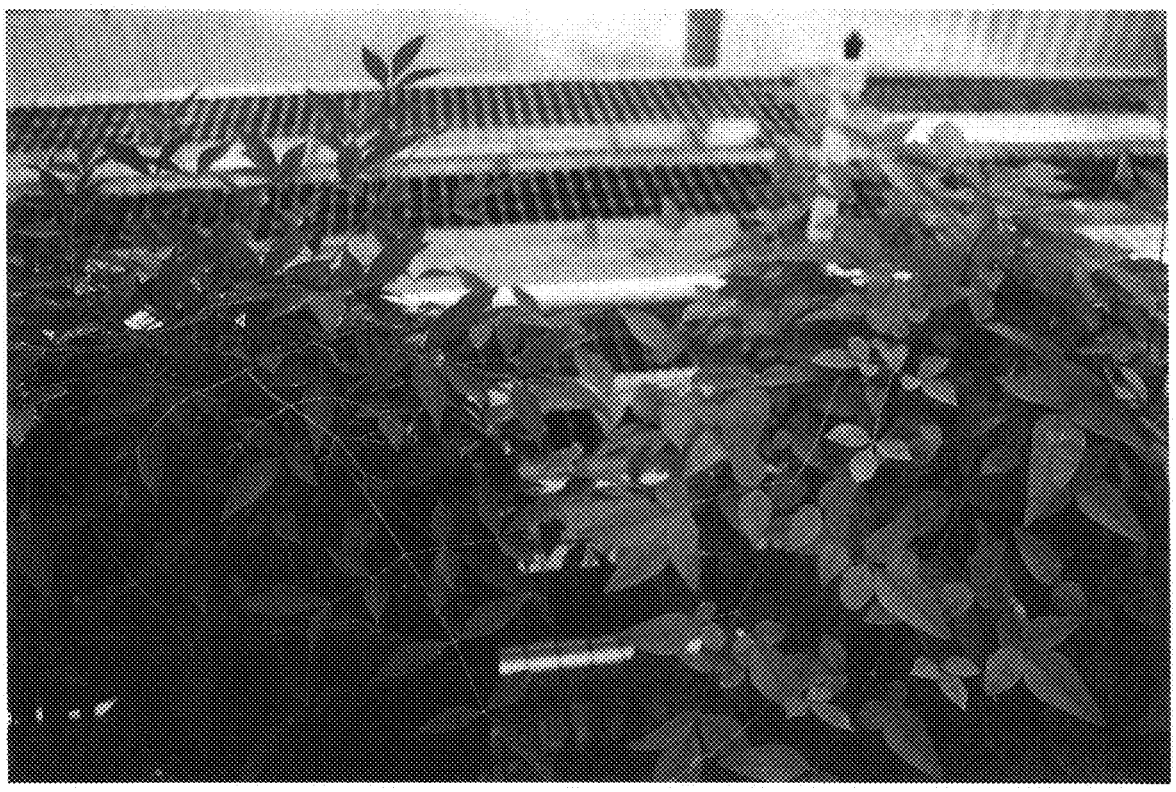
FIG. 3-A

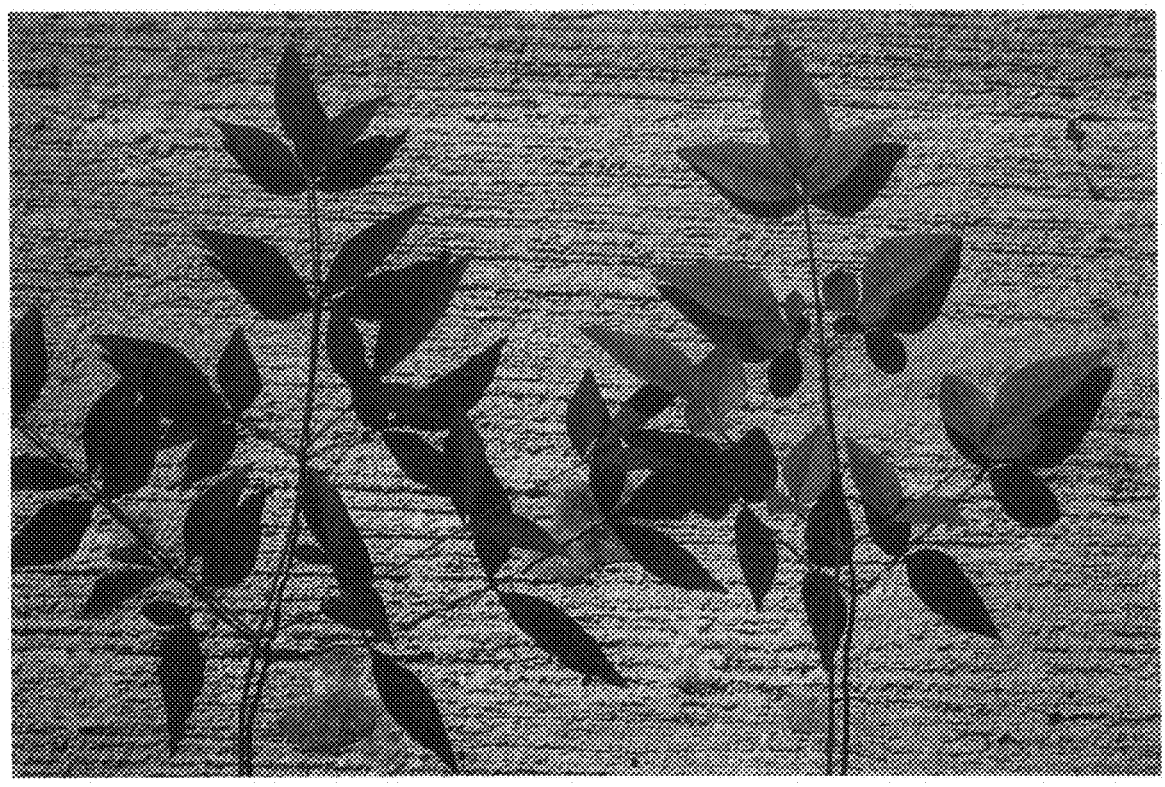
FIG. 3-B

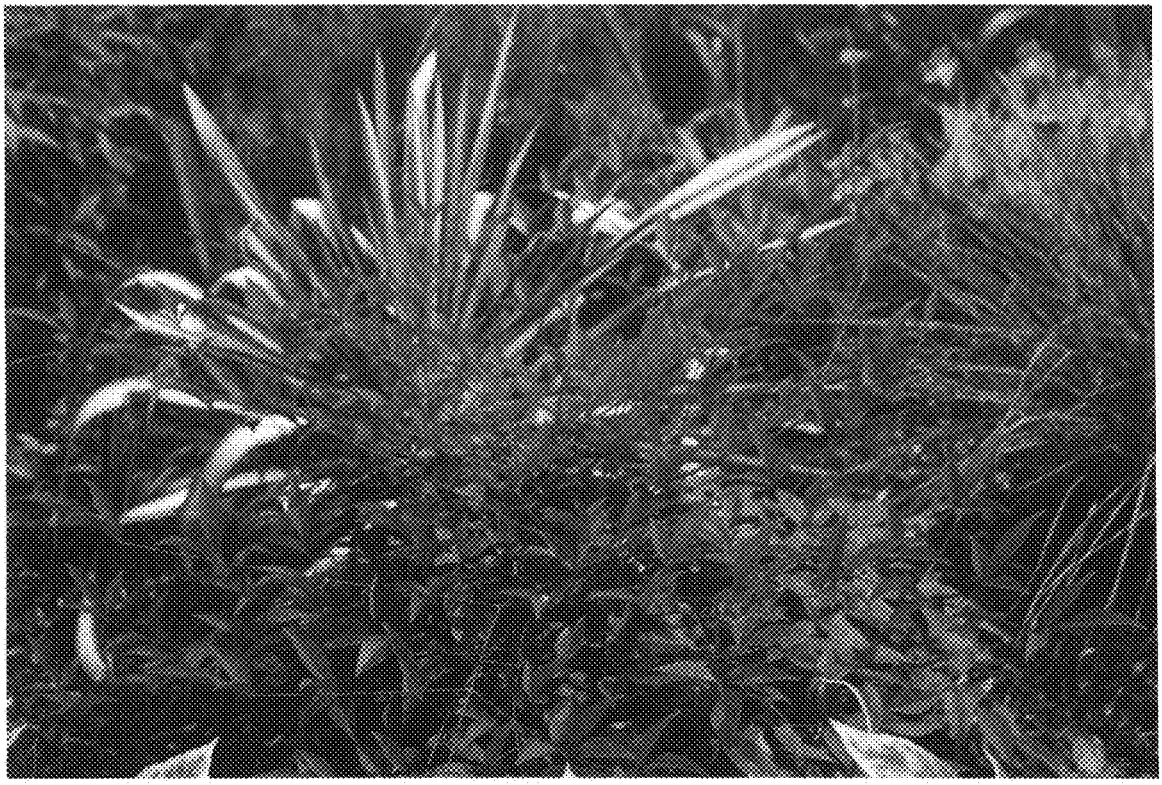
FIG. 4-A

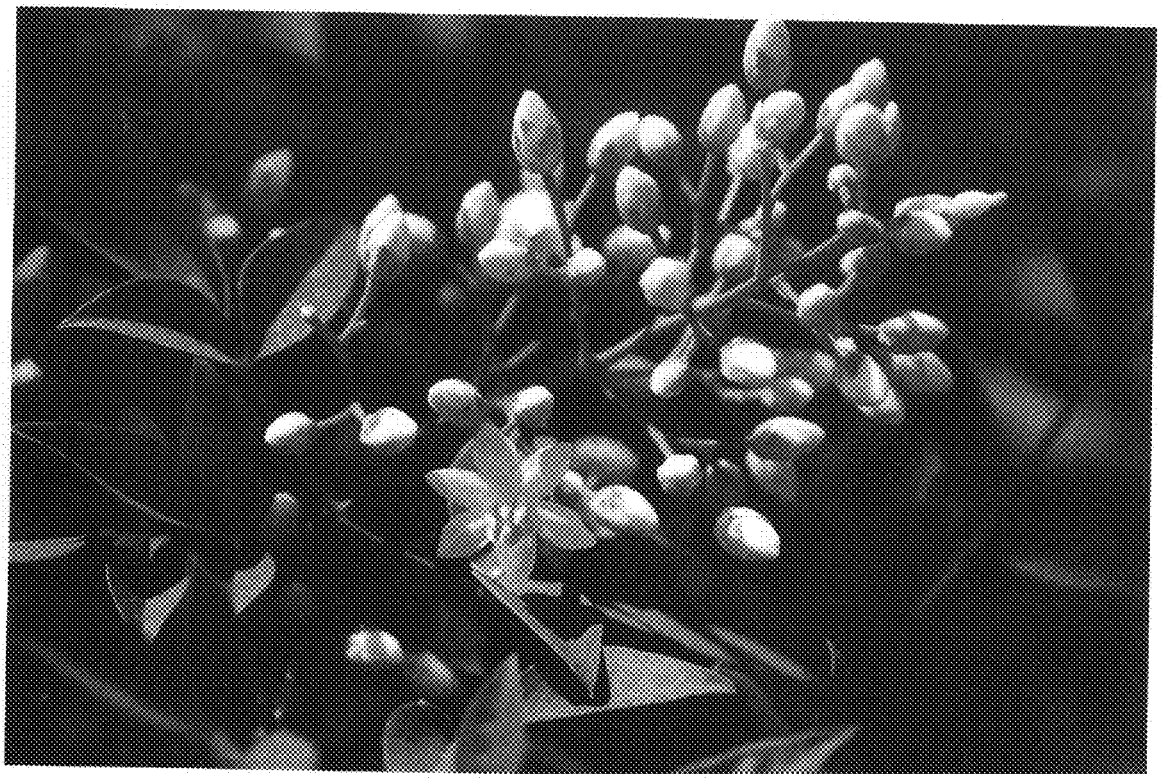
FIG. 5-A